(12) United States Patent
Idelson et al.

(10) Patent No.: US 11,737,661 B2
(45) Date of Patent: *Aug. 29, 2023

(54) WIPER ASSEMBLY FOR IMAGING ELEMENT CLEANING APPARATUS

(71) Applicants: BOARD OF REGENTS, THE UNIVERSITY OF TEXAS SYSTEM, Austin, TX (US); ClearCam Inc., Austin, TX (US)

(72) Inventors: Christopher Idelson, Austin, TX (US); Christopher Rylander, Austin, TX (US); Mitchell Ross Gilkey, Austin, TX (US); James Landon Gilkey, Austin, TX (US)

(73) Assignees: BOARD OF REGENTS, THE UNIVERSITY OF TEXAS SYSTEM, Austin, TX (US); CLEARCAM INC., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/451,418

(22) Filed: Oct. 19, 2021

(65) Prior Publication Data
US 2022/0175236 A1 Jun. 9, 2022

Related U.S. Application Data

(63) Continuation of application No. 17/122,739, filed on Dec. 15, 2020, now Pat. No. 11,172,813, which is a
(Continued)

(51) Int. Cl.
*A61B 1/12* (2006.01)
*A61B 90/70* (2016.01)
*A61B 1/00* (2006.01)

(52) U.S. Cl.
CPC ............ *A61B 1/126* (2013.01); *A61B 1/0008* (2013.01); *A61B 1/00131* (2013.01);
(Continued)

(58) Field of Classification Search
CPC .. A61B 1/00; A61B 1/12; A61B 1/126; A61B 1/127; A61B 1/00087;
(Continued)

(56) References Cited

U.S. PATENT DOCUMENTS 3,832,750 A * 9/1974 Jarvinen .................. B60S 1/60
15/250.16
5,392,766 A * 2/1995 Masterson ............. A61B 1/126
15/244.1
(Continued)

FOREIGN PATENT DOCUMENTS

JP S5861723 A 4/1983
JP H01204637 A 8/1989
(Continued)

OTHER PUBLICATIONS

Office Communication issued in U.S. Appl. No. 16/773,550, dated Nov. 18, 2020.
(Continued)

*Primary Examiner* — Ryan N Henderson
(74) *Attorney, Agent, or Firm* — Parker Highlander PLLC

(57) ABSTRACT

Embodiments of the present invention are directed to providing an effective and reliable approach for cleaning an exposed surface of an imaging element (e.g., a lens) of apparatuses including but not limited to medical imaging instruments such as endoscopes and laparoscopes and the like. In the case of medical imaging instruments, cleaning apparatuses configured in accordance with embodiments the present invention can be cleaned while the distal end portion of the endoscope is in vivo. Such apparatuses have a
(Continued)

cleaning member incorporated therein (e.g., a resilient polymeric wiper, a sponge, an absorbent pad or the like) that is used for cleaning the exposed surface of the imaging element. The apparatus is preferably adapted for being mounted on imaging apparatus but can also be entirely or partially integral with one or more components of the imaging apparatus or system of which it is a component.

14 Claims, 11 Drawing Sheets

Related U.S. Application Data continuation of application No. 16/773,550, filed on Jan. 27, 2020, now Pat. No. 11,013,399.

(52) U.S. Cl.
CPC ...... *A61B 1/00135* (2013.01); *A61B 1/00142* (2013.01); *A61B 90/70* (2016.02); *A61B 1/127* (2013.01)

(58) Field of Classification Search
CPC . A61B 1/00135; A61B 1/00142; A61B 90/70; A61B 2090/701
See application file for complete search history.

(56) References Cited

U.S. PATENT DOCUMENTS

| | | | | |
|---|---|---|---|---|
| 5,518,502 | A * | 5/1996 | Kaplan | A61B 1/127 600/156 |
| 5,860,181 | A * | 1/1999 | Maekawa | B08B 1/007 15/21.1 |
| 6,755,782 | B2 * | 6/2004 | Ogawa | A61B 1/12 600/157 |
| 6,779,383 | B2 * | 8/2004 | Lizotte | G01N 33/18 73/61.48 |
| 6,905,078 | B1 * | 6/2005 | Gattuso | B60S 1/528 239/11 |
| 6,923,759 | B2 * | 8/2005 | Kasahara | A61B 1/00135 600/157 |
| 7,077,803 | B2 * | 7/2006 | Kasahara | A61B 17/00008 600/106 |
| 7,263,997 | B2 * | 9/2007 | Madsen | A61M 16/0833 128/207.14 |
| 7,316,683 | B2 * | 1/2008 | Kasahara | A61B 18/14 606/45 |
| 7,331,971 | B2 * | 2/2008 | Kasahara | A61B 50/30 606/159 |
| 7,485,092 | B1 * | 2/2009 | Stewart | A61B 17/0218 600/176 |
| 7,534,243 | B1 * | 5/2009 | Chin | A61B 18/082 606/49 |
| 7,543,314 | B2 | 6/2009 | Kadykowski | |
| 7,662,164 | B2 * | 2/2010 | Kasahara | A61B 17/320016 606/167 |
| 7,775,970 | B2 * | 8/2010 | Maeda | A61B 1/00135 600/114 |
| 7,867,163 | B2 * | 1/2011 | Chin | A61B 1/313 600/209 |
| 7,959,561 | B2 * | 6/2011 | Akui | A61B 1/00087 600/157 |
| 7,972,265 | B1 * | 7/2011 | Chin | A61B 17/0218 600/206 |
| 7,981,127 | B2 * | 7/2011 | Kasahara | A61B 18/1482 606/190 |
| 8,069,706 | B2 * | 12/2011 | Battefeld | G01N 33/1886 73/61.79 |
| 8,241,210 | B2 * | 8/2012 | Lunsford | A61B 17/3421 600/209 |
| 8,468,642 | B2 * | 6/2013 | Becker | G02B 27/0006 15/250.361 |
| 8,550,988 | B2 * | 10/2013 | Pribanic | A61B 1/00135 600/125 |
| 8,690,764 | B2 * | 4/2014 | Clark | A61B 1/126 600/156 |
| 8,708,889 | B2 * | 4/2014 | Feuer | A61B 17/320016 600/109 |
| 8,979,738 | B2 * | 3/2015 | Hsu | A61B 1/00135 600/122 |
| 9,241,610 | B2 * | 1/2016 | Hsu | A61B 46/10 |
| 9,486,129 | B2 * | 11/2016 | Rodriguez Sanjuan | A61B 1/122 |
| 9,545,194 | B2 * | 1/2017 | Nguyen | A61B 1/00154 |
| 9,632,019 | B2 * | 4/2017 | Karagöz | G01N 21/15 |
| 9,763,567 | B2 * | 9/2017 | O'Prey | A61B 1/126 |
| 9,770,230 | B2 * | 9/2017 | Lau | A61B 1/00089 |
| 9,913,576 | B2 * | 3/2018 | Ray | G02B 27/0006 |
| 10,016,231 | B2 * | 7/2018 | Igarashi | A61B 18/1445 |
| 10,114,216 | B2 * | 10/2018 | Brody | G02B 27/0006 |
| 10,307,041 | B2 * | 6/2019 | Wu | A61B 1/126 |
| 10,349,821 | B2 * | 7/2019 | Gunday | A61B 1/126 |
| 10,595,719 | B2 * | 3/2020 | Hurst | A61B 1/126 |
| 10,791,918 | B1 * | 10/2020 | Gilkey | A61B 90/70 |
| 10,806,337 | B2 * | 10/2020 | Arcot | A61B 1/00098 |
| 2002/0065450 | A1 * | 5/2002 | Ogawa | A61B 1/126 600/157 |
| 2003/0130674 | A1 * | 7/2003 | Kasahara | A61B 17/0218 606/167 |
| 2003/0130675 | A1 * | 7/2003 | Kasahara | A61B 18/1482 606/167 |
| 2003/0139649 | A1 * | 7/2003 | Kasahara | A61B 1/00135 600/157 |
| 2003/0233723 | A1 * | 12/2003 | Lizotte | G02B 27/0006 15/246 |
| 2005/0154257 | A1 * | 7/2005 | Kasahara | A61B 18/1482 600/7 |
| 2005/0159764 | A1 * | 7/2005 | Kasahara | A61B 17/00008 606/159 |
| 2006/0199998 | A1 * | 9/2006 | Akui | A61B 1/00087 600/157 |
| 2008/0306335 | A1 * | 12/2008 | Lau | A61B 1/313 600/106 |
| 2009/0143641 | A1 | 6/2009 | Maeda et al. | |
| 2009/0229067 | A1 * | 9/2009 | Becker | A61B 1/126 15/250.361 |
| 2009/0264703 | A1 * | 10/2009 | Pribanic | A61B 1/00154 604/164.11 |
| 2009/0301175 | A1 * | 12/2009 | Battefeld | G01N 33/1886 73/53.01 |
| 2010/0174144 | A1 * | 7/2010 | Hsu | A61B 1/00135 600/122 |
| 2012/0101337 | A1 * | 4/2012 | Clark | A61B 1/00091 600/157 |
| 2012/0101338 | A1 * | 4/2012 | O'Prey | A61B 1/126 600/157 |
| 2012/0108904 | A1 * | 5/2012 | Ma | A61B 1/126 600/175 |
| 2012/0238816 | A1 * | 9/2012 | Gunday | A61B 1/00135 600/114 |
| 2012/0238818 | A1 * | 9/2012 | O'Prey | A61B 1/126 600/121 |
| 2013/0008466 | A1 | 1/2013 | Karagoz et al. | |
| 2013/0053639 | A1 * | 2/2013 | Ihde, II | A61B 1/3132 600/109 |
| 2013/0150674 | A1 * | 6/2013 | Haig | A61B 1/00135 600/155 |
| 2013/0305469 | A1 * | 11/2013 | Rodriguez Sanjuan | A61B 1/126 15/104.05 |
| 2014/0034082 | A1 * | 2/2014 | Hurst | A61B 1/126 134/8 |
| 2014/0171739 | A1 * | 6/2014 | Nguyen | A61B 1/3132 600/114 |
| 2014/0215736 | A1 * | 8/2014 | Gomez | A61B 1/00135 15/104.05 |
| 2014/0246051 | A1 * | 9/2014 | Hurst | A61B 1/00135 134/8 |

(56) References Cited

U.S. PATENT DOCUMENTS

| | | | |
|---|---|---|---|
| 2014/0249370 A1* | 9/2014 | Hurst | A61B 1/00135 600/114 |
| 2014/0261545 A1* | 9/2014 | Jenkins | A61B 1/00183 134/8 |
| 2015/0190041 A1* | 7/2015 | Suehara | A61B 1/127 600/109 |
| 2015/0196194 A1* | 7/2015 | Wu | A61B 1/00142 600/125 |
| 2015/0201826 A1* | 7/2015 | Hsu | A61B 1/018 600/121 |
| 2015/0216402 A1* | 8/2015 | Ray | A61B 1/00096 600/109 |
| 2015/0282695 A1* | 10/2015 | Tay | A61B 1/126 600/124 |
| 2016/0022367 A1* | 1/2016 | Brody | G02B 27/0006 15/244.4 |
| 2016/0113484 A1* | 4/2016 | Nakaguchi | A61B 1/00048 600/103 |
| 2017/0231689 A1* | 8/2017 | Igarashi | A61B 90/30 600/479 |
| 2017/0311789 A1* | 11/2017 | Mulcahey | A61B 1/126 |
| 2017/0332893 A1* | 11/2017 | Irion | A61B 1/06 |
| 2017/0367571 A1* | 12/2017 | Nave | A61M 16/0463 |
| 2018/0110406 A1* | 4/2018 | Sarnaik | A61B 46/10 |
| 2018/0116496 A1* | 5/2018 | Arcot | H02S 40/36 |
| 2018/0214016 A1* | 8/2018 | Thommen | A61B 1/07 |
| 2018/0344141 A1* | 12/2018 | Rosenbaum | A61B 17/3415 |
| 2020/0060536 A1* | 2/2020 | Rylander | A61B 1/00135 |
| 2021/0219835 A1* | 7/2021 | Lau | A61B 1/3137 |

FOREIGN PATENT DOCUMENTS

| | | |
|---|---|---|
| JP | 04-362912 | 12/1992 |
| JP | H05103748 A | 4/1993 |
| JP | 2007117103 A | 5/2007 |
| WO | WO 2017/006684 | 12/2017 |

OTHER PUBLICATIONS

Office Communication issued in U.S. Appl. No. 17/122,739, dated Apr. 1, 2021.

* cited by examiner

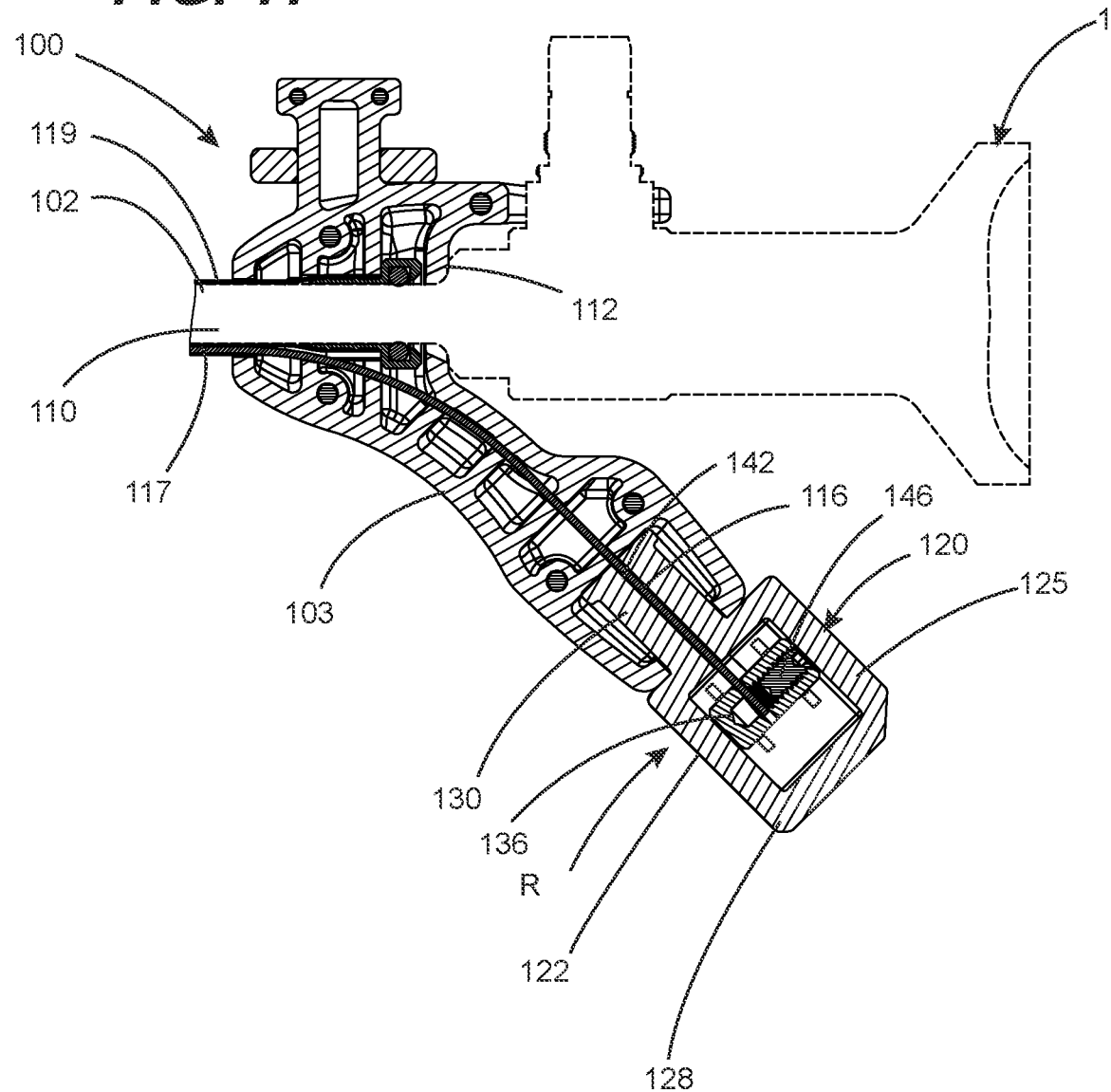

WIPER ASSEMBLY FOR IMAGING ELEMENT CLEANING APPARATUS

This application is a continuation of U.S. patent application Ser. No. 17/122,739, filed Dec. 15, 2020, which is a continuation of U.S. patent application Ser. No. 16/773,550, filed Jan. 27, 2020, now U.S. Pat. No. 11,013,399, each of which is incorporated herein by reference in their entirety.

FIELD OF THE DISCLOSURE

The disclosures made herein relate generally to cleaning of devices that utilize a remote imaging element for visualization of structures at a concealed site and, more particularly, to an imaging element cleaning apparatus for cleaning an exposed surface of the imaging element while the exposed surface is located within a concealed site such as an in vivo human or animal environment, and even more particularly, to wiper assemblies for same.

BACKGROUND

Surgical procedures utilizing in vivo visualization of target surgical sites are well known as a form of a concealed operation site. Examples of these surgeries include, but are not limited to, endoscopic surgery, laparoscopic surgery, thoracoscopic surgery and the like. These surgical procedures all utilize a surgical instrument having an integrated visualization device for providing in vivo visualization of a target surgical site within a surgical space of the patient. Although it is common for the surgical instrument to be referred to in the context of the specific type of surgical procedure (e.g., endoscope for endoscopic surgery, laparoscope for laparoscopic surgery, and the like), these surgical instruments are generally referred to herein as an "endoscope".

As shown in FIG. 1A, an endoscope 1 used in these surgical procedures is characterized as having a user interface portion 5 and an extension portion 10 connected at its proximate end 15 to the user interface portion 5. Scopes for endoscopic surgery generally have an extension portion that is substantially flexible, whereas scopes for other types of surgical procedures—e.g., for laparoscopic surgery, as shown in FIG. 1—generally have an extension portion 10 that is substantially rigid. The extension portion 10 has an imaging element 20 such as a lens at its distal end portion 25. The imaging element 20 can have an exposed surface that is typically generally flush with or that defines an end face of the extension portion 10. The imaging element 20 is connected to an optical fiber or other image transmitting element that is internal to the endoscope. The optical fiber or other image transmitting element extends along the length of the extension portion 10 and terminates at an eyepiece 30 on the user interface portion 5. The eyepiece 30 enables the imaging element 30 to be connected to a visualization device (e.g., a camera connected to a visual display console) through which target surgical sites can be viewed by surgery personnel.

During a surgical procedure using an endoscope, the exposed surface of the imaging element thereof may become impaired due to one or more in vivo scenarios. Examples of these scenarios include the exposed surface of the imaging element becoming fogged with moisture within the surgical space, or the exposed surface of the imaging element may be smeared by blood or other bodily fluids or tissues (e.g. interstitial fluid, fat tissue or the like). Currently, there are two primary different endoscope cleaning methods that are commonly utilized. The first of these cleaning methods is to remove the endoscope from the body, wipe the imaging element clean, and reinsert the endoscope into the body. This method, though effective, is time consuming and causes the surgeon to lose visual of the surgical site, which can be considered dangerous, as surgical instruments typically remain inside the body. This method can also subject the patient to a higher risk of infection. The second of these cleaning methods is to wipe the exposed surface of the imaging element upon a nearby organ or tissue. Although the endoscope remains inside the body, takes less time to clean and does not potentially compromise the surgical site, this method is often not sufficiently effective either due to the "cleaning" surface not providing effective cleaning performance or simply further contaminating the exposed surface of the imaging element. Also, when using either of these cleaning methods, the surgeon must undesirably spend time relocating the endoscope to the surgical site after cleaning the imaging element.

At a minimum, current approaches for cleaning the exposed surface of the imaging element can be a hindrance and an annoyance for surgeons and may offer poor cleaning performance. Additionally, the action of cleaning the exposed surface of the imaging element increases the length of time a surgical procedure takes, thereby decreasing the amount of operating room (OR) time available to the hospital. It is also costly for hospitals, patients, and insurance companies due to wasted time, and possibly surgical complications and post-surgical infection rates. Additionally, as patients undergo longer procedures, their time spent under anesthesia increases. Increased time under anesthesia has been shown to correlate to a rise in surgical complication rates and post-surgical infection rates. Thus, the added time associated with current commonly used approaches for cleaning the exposed surface of the imaging element is not only a hindrance, but also potentially medically and financially costly.

Wiper assemblies of prior art (i.e., conventional) endoscope imaging element cleaning apparatuses are known. FIGS. 6A and 6B (reproduced herein as FIGS. 1B and 1C) of U.S. Pat. No. 6,923,759 discloses a configuration of the wiper assembly of such known prior art endoscope imaging element cleaning apparatuses. As can be seen, this prior art wiper assembly construction is characterized by a single-leg wire attachment, where the wiper rubber 26 (i.e., the wiping member) is mounted on a single leg of wiper rod 25 (i.e., the control element). Notably, no portion of the single leg of the wiper rod 25 encroaches into a cross-sectional area of the resilient wiper rubber 26 that is defined by opposing angled faces of the scraping portion 26A of the wiper rubber 26. Moreover, the overall cross-sectional shape of the wiper rubber 26 and the location of the single leg of the wiper rod 25 within the wiper rubber 26 significantly isolates deflection-defining aspects of the scraping portion 26A from presence of the wiper rod 25 within the wiper rubber 26. As the inventors of the present invention have discovered, such isolation and resulting reliance entirely on bulk material and dimensional properties of the scraping portion 26A limit cleaning efficacy provided by the endoscope imaging element cleaning apparatus and minimization of the physical size of the wiper assembly thereof.

To maintain required visualization of target surgical sites, it is desirable to clean an exposed surface of an imaging element of a device while the distal end portion of the device remains in a concealed operation site (e.g., an endoscope in vivo). Known methods and devices that are intended to provide for cleaning of a surface of such devices when still within the concealed operation site (e.g., an endoscope in vivo) have one or more shortcomings (e.g., lack cleaning efficacy, interfere with the surgical procedure, require significant alteration to a surgeon's preferred surgical technique, etc.). Therefore, an effective, efficient, simple and reliable approach for allowing an exposed surface of an imaging element of device (e.g., an endoscope) to be cleaned while the distal end portion of apparatus is still within the concealed operation site (e.g., in vivo) would be advantageous, desirable and useful.

SUMMARY OF THE DISCLOSURE

Embodiments of the present invention are directed to providing an effective and reliable approach for allowing an exposed surface of an imaging element (e.g., a lens) of a device (e.g., an endoscope) be cleaned while the distal end portion of the device is within a concealed operational site (e.g., in vivo). More specifically, one or more embodiments of the present invention provide an apparatus for use with an endoscope utilized in one or more types of surgical procedures (e.g., endoscopic surgery, laparoscopic surgery, thoracoscopic surgery and the like), Inventive apparatuses as disclosed herein advantageously incorporate a wiper assembly that overcomes shortcomings of prior art endoscope imaging element cleaning apparatuses used for cleaning the exposed surface of the imaging element of the device while the imaging element is within the concealed operation site. Such apparatuses are preferably adapted for having the device mounted thereon but can also be can be entirely or partially integral with one or more components of the device (e.g., a robotic arm configured for carrying, operating and manipulating an endoscope).

Advantageously, cleaning apparatuses configured in accordance with embodiments of the present invention can include a wiper assembly characterized by a portion of a coupling element (e.g., a wire) of the wiper assembly at least partially encroaching into a portion of a cleaning member (i.e., resilient wiper body) of the wiper assembly that is defined by opposing angled faces of a blade portion of the cleaning member. In one or more embodiments, such portion of the coupling element of the wiper assembly preferably resides entirely within the cross-sectional area of the cleaning element that is defined by the opposing angled faces of the blade portion of the cleaning member. In this respect, the inventive construction of the wiper assembly of cleaning apparatuses in accordance with embodiments of the present invention have a cleaning member with an overall cross-sectional shape and a coupling element location within the cleaning member that achieves deflection-defining aspects of the blade portion of the cleaning member as a function of both the cleaning member material and presence of at least a portion of the coupling element within the blade portion of the cleaning member. As the inventors of the present invention have discovered, such integration of the cleaning member material and presence of the portion of the coupling element therein provides a resulting synergistic functionality. This resulting synergistic functionality leverages the bulk material and dimensional properties of the wiper assembly to enable a superior degree and reliability of cleaning efficacy provided by the endoscope imaging element cleaning apparatuses in accordance with embodiments of the present invention and minimization of the physical size of the wiper assemblies thereof.

In one or more embodiments of the present invention, an in vivo endoscope cleaning apparatus comprises a chassis, a coupling element and a cleaning member. The chassis is adapted for having an endoscope mounted thereon. The coupling element is movably attached to the chassis. The coupling element has a proximate end portion adjacent to a proximate end portion of the chassis and a distal end portion adjacent to a distal end portion of the chassis. The coupling element includes a cleaning member engaging structure at the distal end portion thereof. The cleaning member engaging structure is retained within the cleaning member whereby movement of the coupling element causes a corresponding movement of the cleaning member. The cleaning member includes opposing angled faces defining a blade portion thereof. At least a portion of the cleaning member engaging structure is located within the blade portion.

In one or more embodiments of the present invention, an in vivo endoscope cleaning apparatus comprises a chassis, a coupling element and a cleaning member. The chassis is adapted for having an endoscope mounted thereon. The coupling element is movably attached to the chassis. The coupling element has a proximate end portion adjacent to a proximate end portion of the chassis and a distal end portion adjacent to a distal end portion of the chassis. The coupling element includes a cleaning member engaging structure at the distal end portion thereof. The cleaning member engaging structure includes a U-shaped portion defining a first leg portion of the cleaning member engaging structure and a second leg portion of the cleaning member engaging structure. The cleaning member engaging structure is member within the cleaning member whereby movement of the coupling element causes a corresponding movement of the cleaning member. The cleaning member includes opposing angled faces defining a blade portion thereof. An entire portion of the first leg portion is located within the blade portion.

In one or more embodiments of the present invention, an in vivo endoscope cleaning apparatus comprises an elongated body, a cleaning member, a user interface body, a coupling element and a cleaning member control mechanism. The elongated body includes a central passage adapted for having an extension portion of an endoscope seated therein. A distal end portion of the elongated body has an opening therein through which an imaging element attached to the extension portion of the endoscope is accessible when the extension portion of the endoscope is in a seated configuration within the central passage of the elongated body. The cleaning member is adjacent to the opening at the distal end portion of the elongated body. The cleaning member includes a main body and a blade portion extending from the main body. The blade portion is defined by opposing angled faces. The user interface body is connected to a proximate end of the elongated body. The coupling element is fixedly attached at a distal end portion thereof to the cleaning member. The coupling element includes a cleaning member engaging structure at the distal end portion thereof. The cleaning member engaging structure is retained within the cleaning member. At least a portion of the cleaning member engaging structure is located within the blade portion of the cleaning member. The cleaning member control mechanism is movably mounted on the user interface body. A first cleaning member manipulation mode of the cleaning member control mechanism enables the cleaning member to be moved between a stowed position and a use position relative to the distal end portion of the elongated body and a second cleaning member manipulation mode of the cleaning member control mechanism enables the cleaning member to be moved into or away from contact with the imaging element while the cleaning member is in the use position.

In one or more embodiments, the cleaning member engaging structure includes a plurality of segments that are spaced apart from each other and an entire portion of a first one of the segments of the cleaning member engaging structure is within the blade portion.

In one or more embodiments, a second one of the segments of the cleaning member engaging structure defines a distal end face of the distal end portion of the coupling element and an entire portion of the second one of the segments of the cleaning member engaging structure is within the main body.

In one or more embodiments, the first and second ones of the segments of the cleaning member engaging structure extend generally parallel to each other.

In one or more embodiments, the blade portion has a triangular cross-sectional shape and the cleaning member engaging structure has a round cross-sectional shape.

In one or more embodiments, a diameter of the first one of the segments of the cleaning member engaging structure is at least about 40% of an overall length of the blade portion.

In one or more embodiments, the opposing angled faces defining the blade portion extend generally perpendicular to each other and a reference axis extends through a centerline cross-sectional axis of the first one of the segments of the cleaning member engaging structure, through a centerline cross-sectional axis of the second one of the segments of the cleaning member engaging structure and through an intersecting point of the opposing angled faces.

In one or more embodiments, the reference axis bisects the cleaning member.

In one or more embodiments, the reference axis is characterized by at least one of extending generally parallel to a longitudinal axis of a portion of the control element extending between the proximate and distal end portions of the chassis and residing within a plane within which the longitudinal axis of the portion of the control element extending between the proximate and distal end portions of the chassis resides.

These and other objects, embodiments, advantages and/or distinctions of the present invention will become readily apparent upon further review of the following specification, associated drawings and appended claims.

BRIEF DESCRIPTION OF THE DRAWINGS

FIG. 11 is a cross-sectional view taken along the line 11-11 in FIG. 2.

DETAILED DESCRIPTION

Figure 1A:
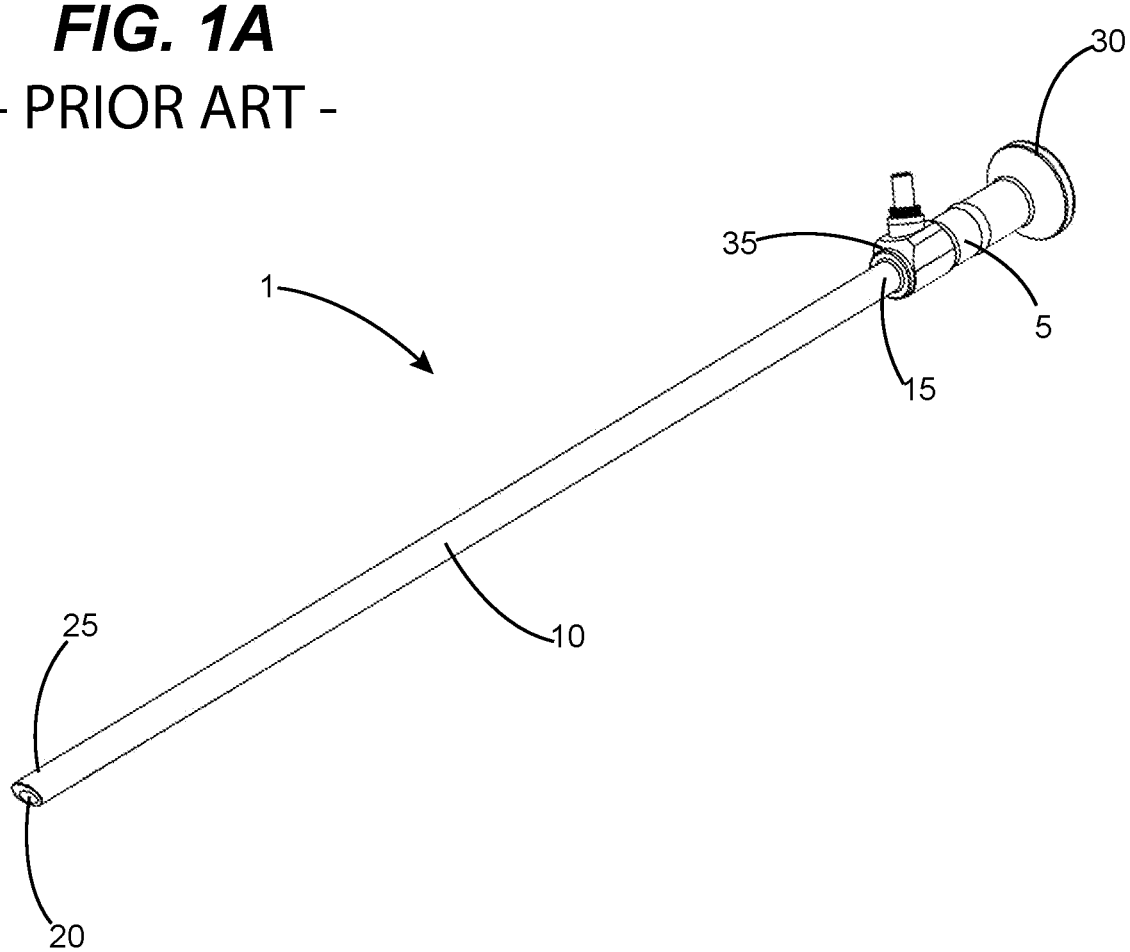
FIG. 1A is a perspective view showing a prior art endoscope.
Figure 1B:
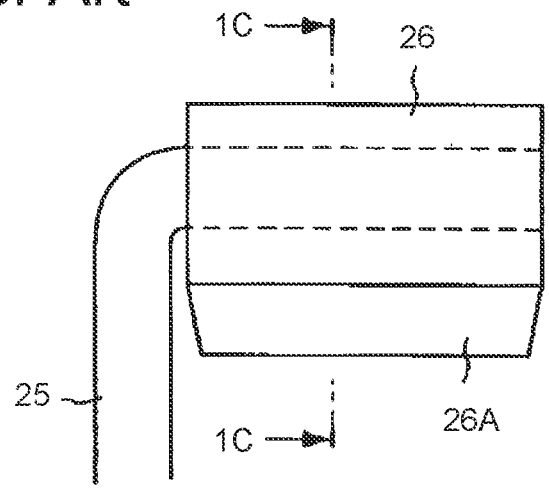
FIG. 1B is a plan view showing a prior art wiper assembly.
Figure 1C:
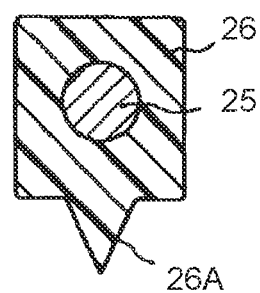
FIG. 1C is a cross-sectional view taken along the line 1C-1C in FIG. 1B.

FIGS. 2-10 illustrate various aspects of an in vivo endoscope cleaning apparatus configured in accordance with a first embodiment of the present invention, which is designated as cleaning apparatus 100. Cleaning apparatus 100 is preferably, but not necessarily, configured to be used with commercially available endoscopes, such as endoscope 1 of FIG. 1. Examples of such commercially available endoscopes include, but are not limited to, endoscopes manufactured under brand names of Karl Storz, Linvatec, Olympus, Richard Wolf, Stryker and Intuitive Surgical (i.e., DaVinci). To this end, in preferred embodiments, cleaning apparatus 100 can be engineered as endoscope-specific for a given model(s) of one or more manufacturers based on the dimensional attributes of such commercially available endoscopes. An underlying consideration of the manner in which the endoscope cleaning apparatus 100 is engineered for an intended brand(s) or model(s) of endoscope is that there be a high level of dimensional precision between the endoscope and the cleaning apparatus. Such dimensional precision can be characterized to include both the inhibition of any unacceptable level of relative movement between the endoscope and the cleaning apparatus 100 and relative placement of key structural elements of the endoscope relative to those of the cleaning apparatus 100.

Figure 2:
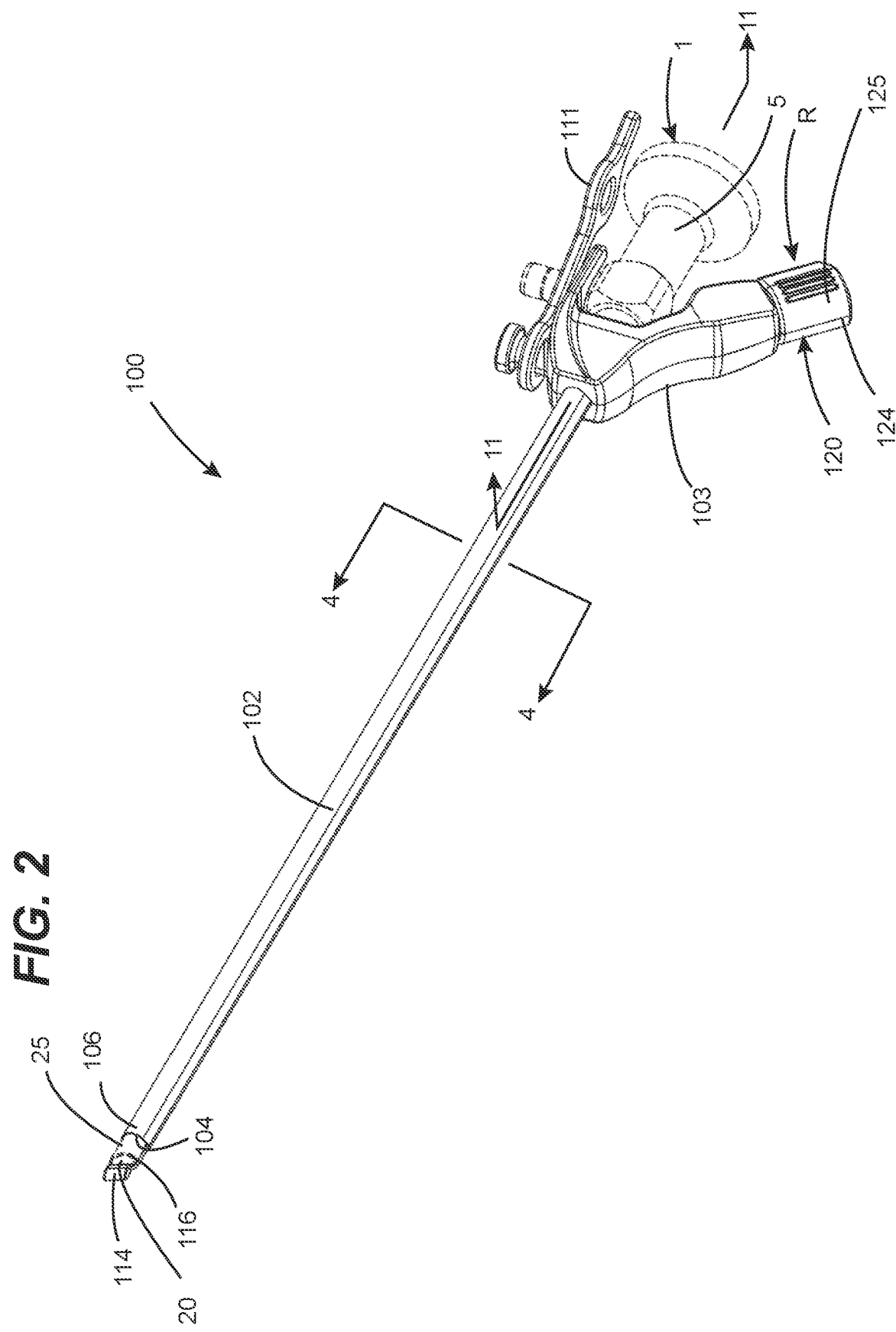
FIG. 2 is a first perspective view showing an endoscope cleaning apparatus in accordance with a first embodiment of the present invention.
Figure 3:
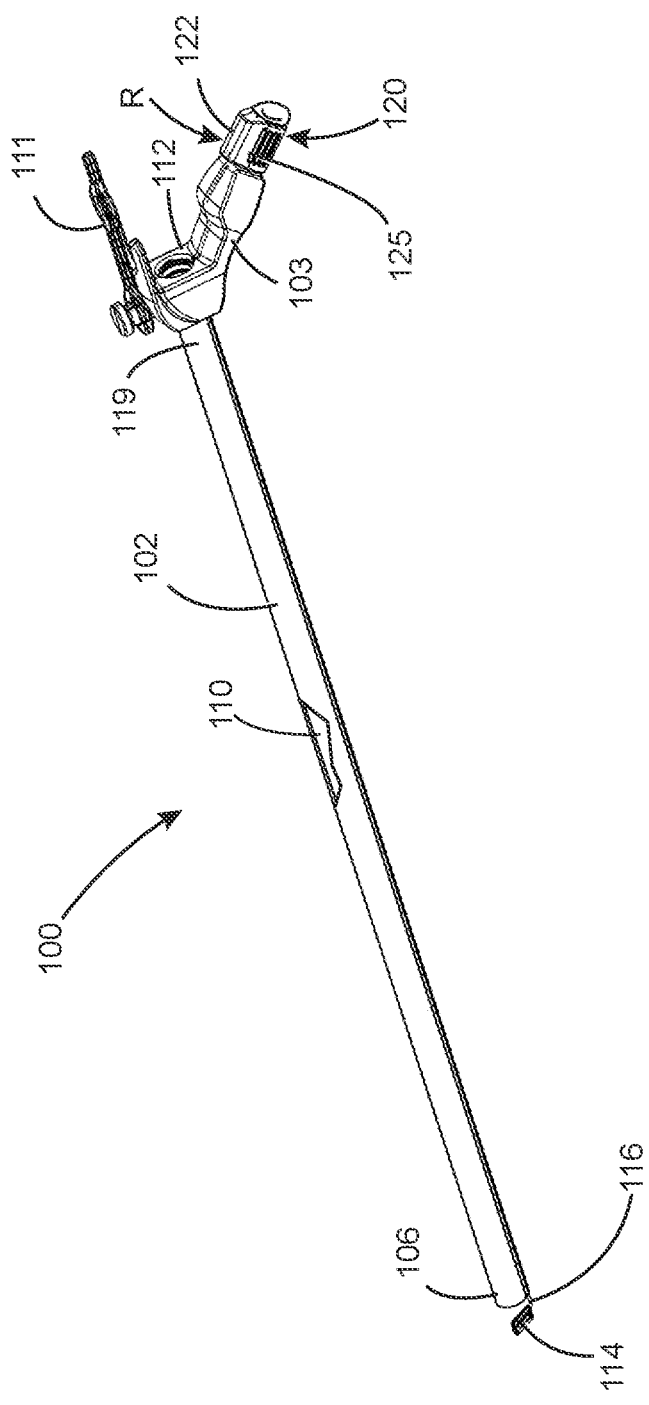
FIG. 3 is a second perspective view showing the endoscope of FIG. 2.

Still referring to FIG. 2, the cleaning apparatus 100 has an elongated body 102 that is adapted to have the extension portion 10 of the endoscope 1 inserted. In its fully seated placement, as shown, a dimensionally predictable surface or feature of the endoscope 1 such as that of the user interface portion 5 (e.g., a handle and/or optic interface portion) abuts a mating dimensionally predictable surface or feature of the endoscope cleaning apparatus 100. This mating surface or feature of the cleaning apparatus 100—such as a surface or feature of a user interface body 103 thereof—serves as a reference structure of the cleaning apparatus 100. With the endoscope 1 in this fully seated position on the cleaning apparatus 100 with respect to the reference structure, a distal end portion 25 of the endoscope protrude from within an opening 104 in the distal end portion 106 of the elongated body 102 by a known, predictable amount. Through such an interfacial arrangement and dimensional tolerances, a high level of dimensional precision between the endoscope 1 and the cleaning apparatus 100 can be achieved. As discussed below in greater detail, such dimensional precision is beneficial to the cleaning performance afforded by the cleaning apparatus 100.

As discussed above in reference to FIG. 1, the distal end portion 25 of the endoscope 1 carries the imaging element 20 (e.g., a lens). The imaging element 20 is exposed at and is generally flush with or defines an end face at the distal end portion 25 of the extension portion 10 of the endoscope 1. The distal end portion 25 of the endoscope 1 is exposed at an opening 104 in a distal end 106. As a result of the seated placement of the endoscope 1 on the cleaning apparatus 100, the imaging element 20 is at a known and predictable position relative to the reference structure of the cleaning apparatus 100. Thus, for an endoscope engineered for use with a specific cleaning apparatus, the components of the cleaning apparatus 100 can similarly be at known and predictable position relative to structures of the endoscope 1, thereby providing for precise placement and configuration of components of the cleaning apparatus 100 to achieve a desired and predictable level of cleaning performance.

Referring now to FIGS. 3-6, the elongated body 102 and the user interface body 103 jointly define a chassis of the cleaning apparatus. The chassis serves as the platform on which the endoscope 1 can be mounted in a predictable seated position. It is disclosed herein that the chassis can be that of a robot that provides robot-assisted surgery or can be adapted to operatively interface with a mating mounting portion of such a robot. For example, the elongated body 102 and/or the user interface body 103 can be that of an arm or other structure of the robot or adapted to operatively interface with an instrument mounting portion of the arm of the robot.

The elongated body 102 of the chassis can be a tube having a central passage 110 (shown in FIG. 3) with a round or generally round cross-sectional shape. The central passage 110 has a size and profile that is adapted to have the extension portion 10 of the endoscope 1 seated therein by inserting the extension portion into the central passage 110 and sliding the extension portion 10 along the length of the elongated body 102 until the endoscope 1 is in a seated position on the chassis. The user interface body 103 can include a retention tool 111 for securing the endoscope 1 is in the seated position on the chassis. Alternatively, the elongated member 102 can be a non-tubular structure such as a skeletal structure that engages the extension portion 10 of the endoscope at discrete spaced-apart locations thereof.

The chassis can include a plurality of structural elements that provide for the known and predictable position of the endoscope 1 when mounted in a seated position on the chassis. One of these structural elements is the effective inside diameter (e.g., for ribbed or textured interior surface) or the actual inside diameter (e.g., a smooth interior wall) of the elongated body 102 in relation to an outside diameter of the extension portion 10 of the endoscope 1 and the elongated body 102 of the chassis. It is preferable to maintain a close fit between the outside wall of elongated body 102 and the mating exterior wall of the extension portion 10 so as to provide for a fluid-resistant interface between the elongated body 102 and the extension portion 10 and to limit off-axis pitch between a longitudinal axis of the elongated body 102 and the extension portion 10. Another one of these structural elements is a seating surface 112 (shown in FIGS. 3 and 11) on the user interface body 103. The seating surface can be a reference surface of the cleaning apparatus 100 that engages a mating reference surface 35 (shown in FIG. 1) of the endoscope 1. Engagement of the seating surface 112 on the user interface body 103 with the mating reference surface 35 of the endoscope 1 serves to define a predictable seated orientation of the endoscope 1 on the chassis.

Figure 4:
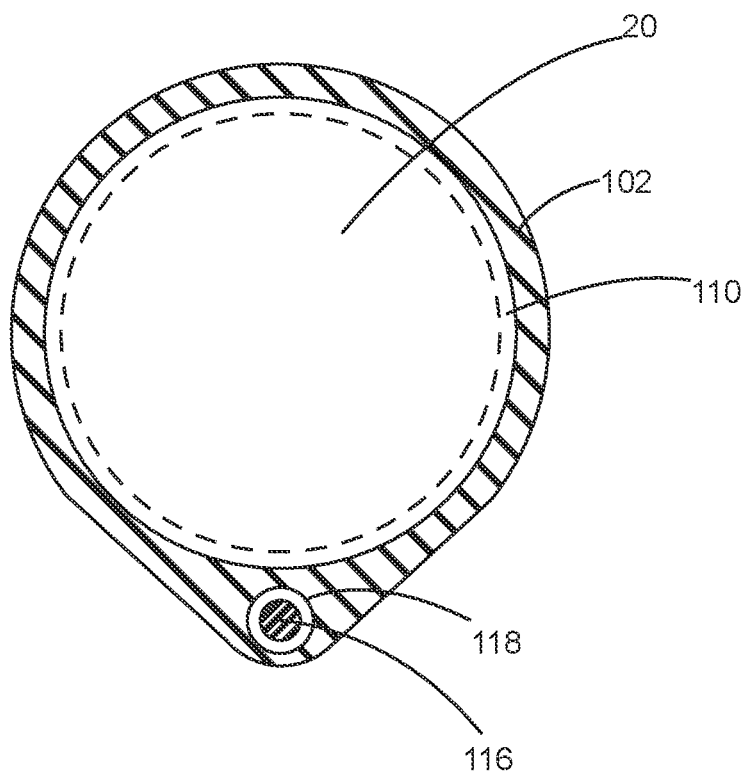
FIG. 4 is a cross-sectional view taken along the line 4-4 in FIG. 2.

The cleaning apparatus 100 includes a cleaning member 114 (shown in FIGS. 2 and 3) adjacent to the opening 104 in the distal end portion 106 of the elongated body 102. As discussed below in greater detail, the cleaning member 114 functions to clean contaminants and debris from a surface of the imaging element 20 when brought into contact with the imaging element 20 of the endoscope. The cleaning member 114 can be fixedly attached to a distal end portion of a coupling element 116. As best shown in FIG. 4, the coupling element 116 extends through a channel 118 within the elongated body 102. Preferably, the channel 118 and the central passage 110 extend substantially parallel to each other within the elongated body 102. In some embodiments, the coupling element 116 is characterized by an elongated small diameter structure that offers at least a limited degree of bendability in combination with high torsional rigidity. In other embodiments, the coupling element 116 is characterized by an elongated small diameter structure that offers a given amount of torsional compliance. Based on these characterizing attributes, examples of coupling element 116 include, but are not limited to, solid metallic wire, spiraled metal wire, a polymeric filament(s), a composite filament(s) or the like.

Figure 6:
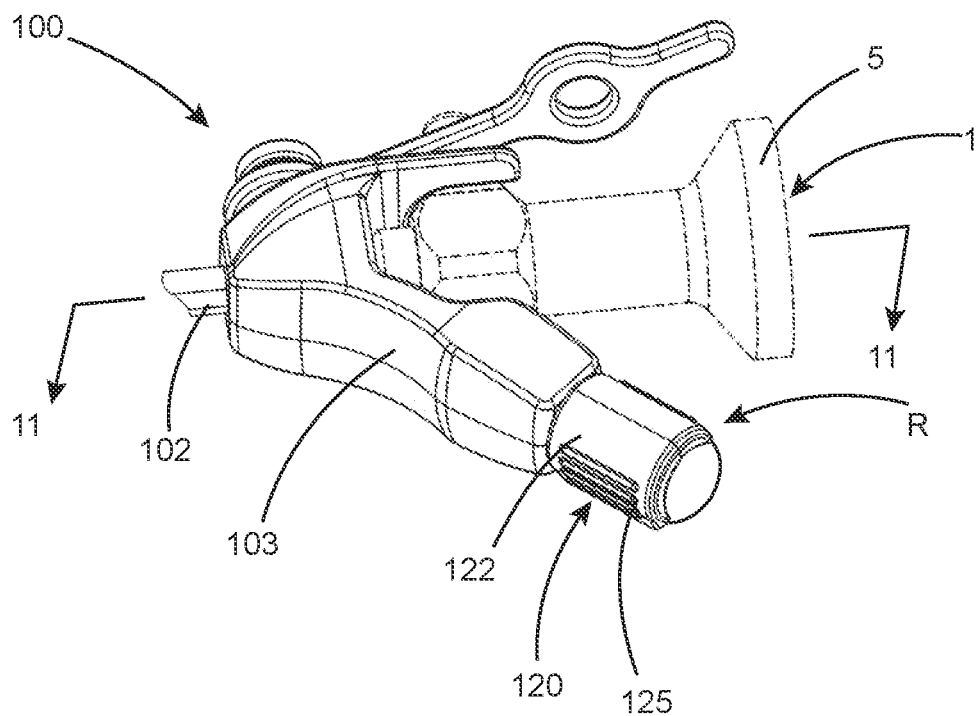
FIG. 6 is partial perspective view of the endoscope cleaning apparatus shown in FIG. 2, where a control body of a first cleaning member control mechanism is in a retracted configuration.
Figure 5:
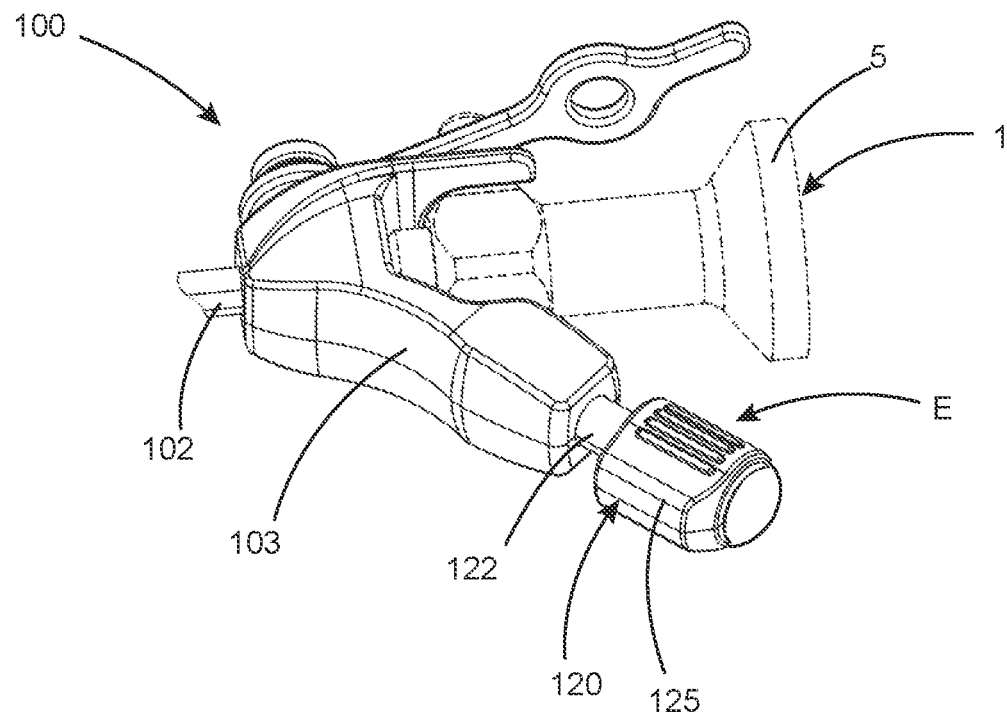
FIG. 5 is partial perspective view of the endoscope cleaning apparatus shown in FIG. 2, where a control body of a first cleaning member control mechanism is in an extended configuration.
Figure 7:
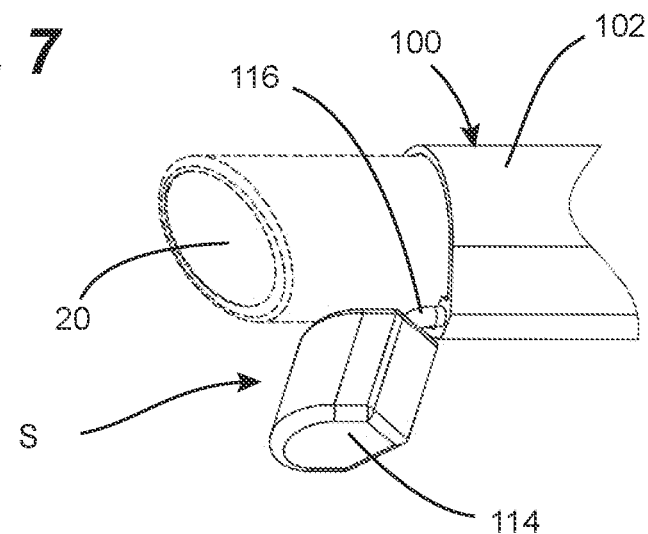
FIG. 7 is partial perspective view of the endoscope cleaning apparatus shown in FIG. 2, where a cleaning member thereof is in a stowed position.
Figure 8:
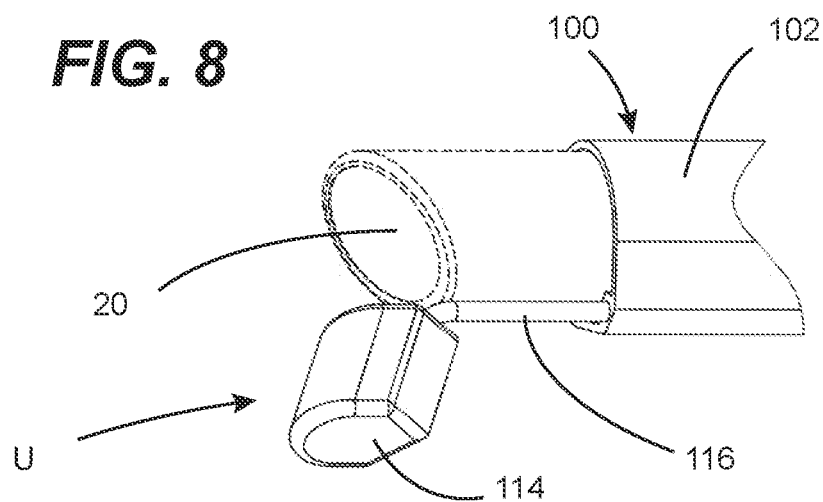
FIG. 8 is partial perspective view of the endoscope cleaning apparatus shown in FIG. 2, where the cleaning member thereof is in a use position.
Figure 9:
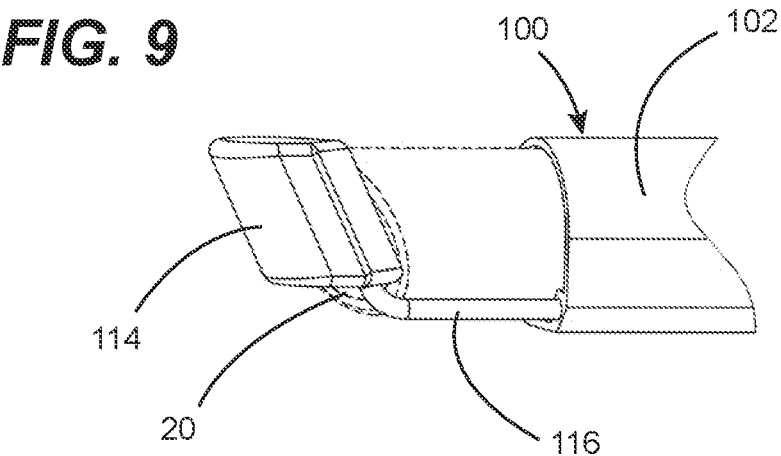
FIG. 9 is partial perspective view of the endoscope cleaning apparatus shown in FIG. 2, where the cleaning member thereof is moved to an imaging element contacting position thereof.
Figure 12:
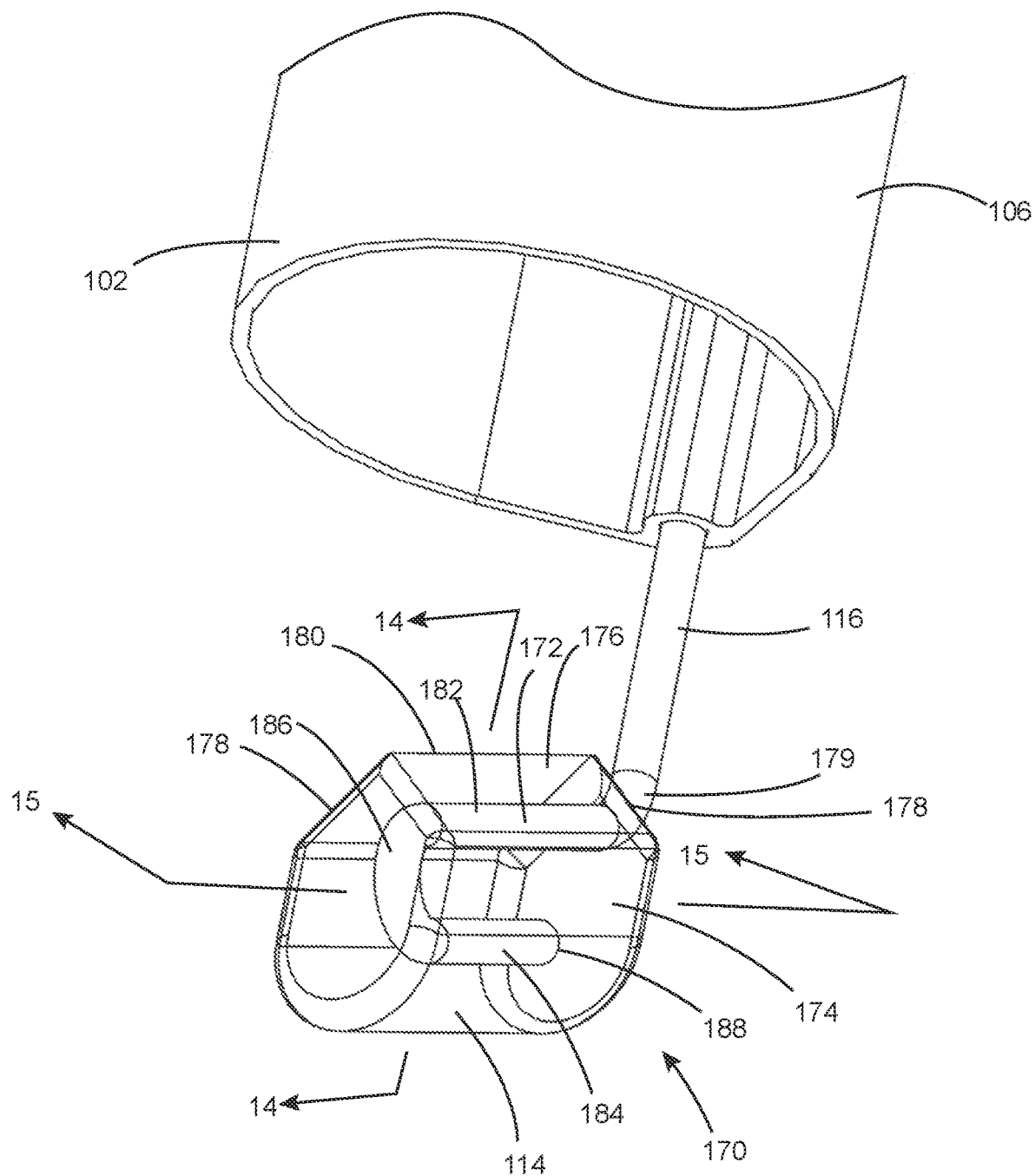
FIG. 12 is a first perspective view showing a wiper assembly configured in accordance with an embodiment of the present invention.
Figure 13:
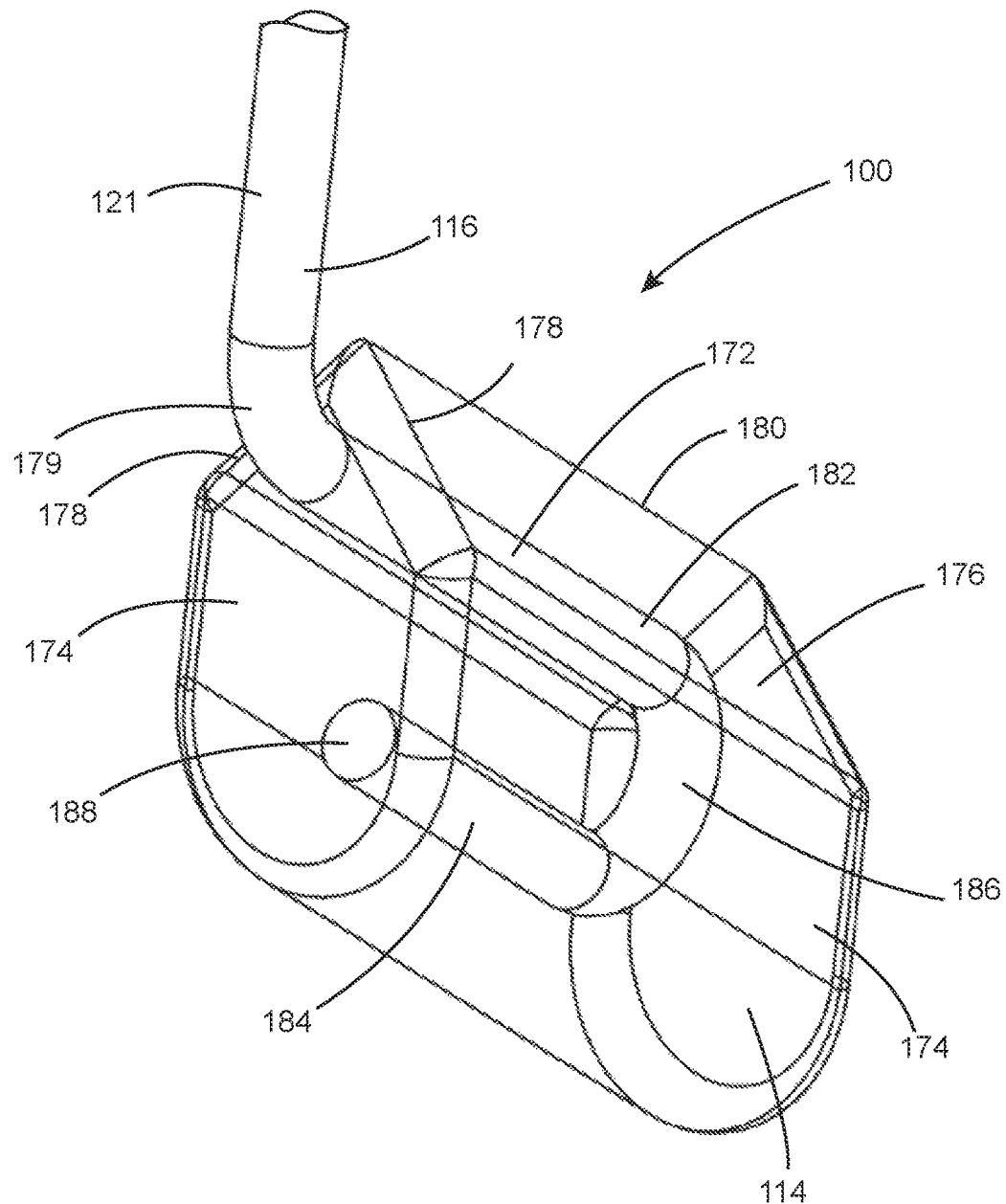
FIG. 13 is a second perspective view showing the wiper assembly of FIG. 12.

The user interface body 103, which can be configured as a handle for the cleaning apparatus 100, carries a cleaning member controller 120. The cleaning member controller 120 is coupled between the user interface body 103 and the cleaning member 114 for enabling selective movement of the cleaning member 114. The cleaning member controller 120 includes a first cleaning member control mechanism 122 (i.e., a cleaning member movement mechanism). The first cleaning member control mechanism 122 includes a control body 125 (i.e., the first control body 125) that is rotatably and translatably mounted on (i.e., attached to) the user interface body 103, as best shown in FIGS. 5 and 6. The first cleaning member control mechanism 122 provides for various cleaning member manipulation modes.

Through such movement capability of the first cleaning member control mechanism 122, the first cleaning member control mechanism provides at least a first cleaning member manipulation mode and a second cleaning member manipulation mode. The first cleaning member manipulation mode can include translational movement, as provided for by translation of the coupling element 116 to move the cleaning member 114 between a stowed position S (best shown in FIG. 7) and a use position U (best shown in FIG. 8)—i.e., the first cleaning member manipulation mode. As can be seen, the stowed position S and the use position U are relative to a location of the imaging element 20 of the endoscope 1 when the endoscope 1 is mounted on the chassis. The use position U is a position in which the cleaning member 114 is beyond a terminal end of the endoscope 1. The stowed position S is a position in which the cleaning member 114 is retracted from the use position U (e.g., by a maximum distance of travel therebetween). The second cleaning member manipulation mode can include rotational movement to move the cleaning member 114 into and away from contact with the imaging element 20 (as best shown in FIGS. 6 and 8-10) while the cleaning member 114 is in the use position—i.e., the second cleaning member manipulation mode or, as discussed below, an offset use position adjacent thereto. In this manner, the first cleaning member manipulation mode of the first cleaning member control mechanism 122 permits manipulation of the cleaning member 114 for enabling in vivo cleaning of the imaging element 20 in concert with in vivo surgical cavity visualization utilizing the imaging element 20.

Referring now, to FIG. 11, aspects of a specific implementation of the cleaning member control mechanism 122 is described. The first control body 125 includes a user interface portion 128 and a mounting portion 130 connected to the user interface portion 128. The mounting portion 130 is translatably and rotatably attached to a mating portion of the user interface body 103. For example, the mounting portion 130 can include a cylindrical extension portion that is seated in a mating passage of the user interface body 103 to permit the first cleaning member control mechanism 122 to be axially translated relative to the user interface body 103 between an extended position E (FIG. 5) and a retracted position R (FIG. 6) for correspondingly moving the cleaning member 114 between the stowed position S and the use position U, and to be rotationally translated relative to the user interface body 103 for correspondingly moving the cleaning member 114 into and away from contact with the imaging element 20 of the endoscope 1. Dimensions of the mounting portion 130 and the mating passage of the user interface body 103 can jointly define the amount of translational movement that the cleaning member control mechanism 122 exhibits.

Still referring to FIG. 11, a coupling element engaging structure 136 is disposed on the first control body 125 so as to inhibit axial translation of the coupling element engaging structure 136 relative to the first cleaning member control mechanism 122 and to inhibit unrestricted rotational movement therebetween (i.e., a rotation-inhibiting, translation-enabling interface). For example, the coupling element engaging structure 136 can have an oblong lateral shape (e.g., rectangular) and be located within a mating elongated cavity of the first control body 125 that has an oblong lateral shape, with mating surfaces of the coupling element engaging structure 136 and the first control body 125 being configured to inhibit relative translational and rotation movement therebetween.

Referring now to FIGS. 12-15, various aspects of a wiper assembly 170 of the cleaning apparatus 100 discussed above in reference to FIGS. 2-11 are discussed. The wiper assembly 170 provides for effective and reliable cleaning of an exposed surface of the imaging element 20 of the endoscope 1 (FIGS. 2 and 7-10) to be cleaned while the distal end portion of the endoscope 1 is within a concealed operational site (e.g., in vivo). Through extensive experimental effort, the inventors have discovered that the construction of wiper assemblies of cleaning apparatuses in accordance with embodiments of the present invention provide superior cleaning efficacy as compared to conventional wiper assembly constructions and, thus, makes such cleaning apparatuses similarly superior to conventional endoscope imaging element cleaning apparatuses.

The wiper assembly 170 includes the cleaning member 114 and the coupling element 116. The coupling element 116 has a proximate end portion 117 adjacent to a proximate end portion 119 of the chassis of the cleaning apparatus 100 (i.e., the proximate end portion of the elongated body 102), as shown in FIG. 11. The coupling element 116 has a distal end portion 121 adjacent to a distal end portion 106 of the chassis of the cleaning apparatus 100 (i.e., the distal end portion of the elongated body 102), as shown in FIGS. 19 and 20.

Still referring to FIGS. 12-15, the coupling element 116 includes a cleaning member engaging structure 172 at its distal end portion 121. The cleaning member engaging structure 172 is captured within the cleaning member 114. For example, in preferred embodiments, the cleaning member 114 can be molded onto the cleaning member engaging structure 172. In this respect, movement of the coupling element 116 causes a corresponding movement of the cleaning member 114 that enables cleaning of the imaging element 20 of the endoscope 1.

The cleaning member 114 has a main body 174 and a blade portion 176 extending from the main body 174. The blade portion 176 is defined by opposing angled faces 178. An intersecting point of the opposing angled faces 178 defines a wiping edge 180 of the cleaning member 114 that engages the imaging element 20 of the endoscope 1. In preferred embodiments, the opposing angled faces 178 defining the blade portion 176 extend generally perpendicular to each other (i.e., 90-degrees) and create a sharp edge (e.g., radius of less than about 0.010 inches). In other embodiments, the opposing angled faces 178 can extend relative to each other at an angle greater than or less than 90-degrees.

Figure 10:
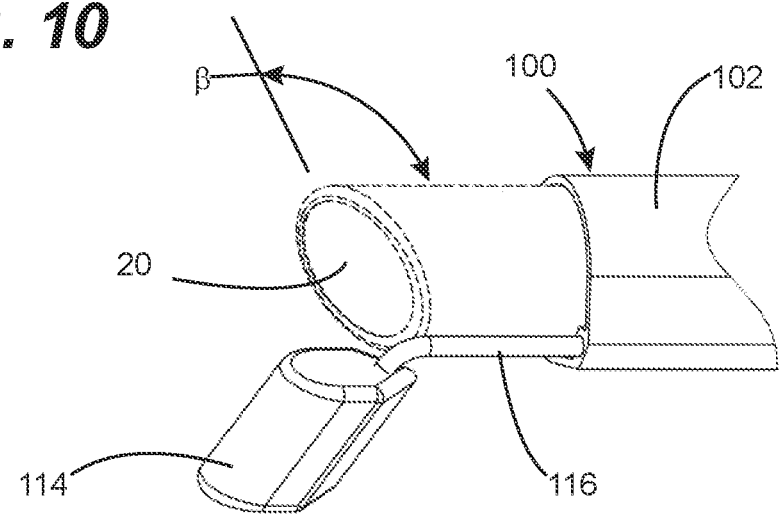
FIG. 10 is partial perspective view of the endoscope cleaning apparatus shown in FIG. 2, where the cleaning member thereof is moved beyond the imaging element contact position thereof.

The cleaning member 114 and the coupling element 116 can be individually constructed and/or jointly configured such that a wiper edge angle $\alpha$ (FIG. 15) is nominally the same as an imaging element angle $\beta$ (FIG. 10). Examples of the imaging element angle $\beta$ of commercially available endoscopes include, but are not limited to, 90 degrees and 120 degrees. To promote cleaning efficacy via loading and/or displacement of the blade portion 176 of the cleaning member 114 in response to being brought into contact with the imaging element 20 of the endoscope 1, the wiper edge angle $\alpha$ can be slightly less the than the imaging element angle $\beta$ of a corresponding endoscope intended to be used therewith. To this end, a bend 179 of the coupling element 116 between the cleaning member 114 and the elongated member 102 can be bent to have a coupling element bend angle $\theta$ slightly less than the imaging element angle $\beta$ (e.g., 2-5 degrees less), the wiper edge angle $\alpha$ can be slightly less than the imaging element angle $\beta$ and/or the cleaning member 114 can be attached to the coupling element 116 in a manner such that the wiper edge angle $\alpha$ is slightly less than the imaging element angle $\beta$.

The cleaning member engaging structure 172 preferably has a U-shaped portion defining a first leg portion 182, a second leg portion 184 and an arcuate segment 186 extending therebetween. In this respect, the cleaning member engaging structure 172 includes a plurality of segments that are spaced apart from each other. As shown, the first leg portion 182 and the second leg portion 184 extend generally parallel to each other. The second leg portion 184 can defines a distal end face 188 of the coupling element 116.

Figure 14:
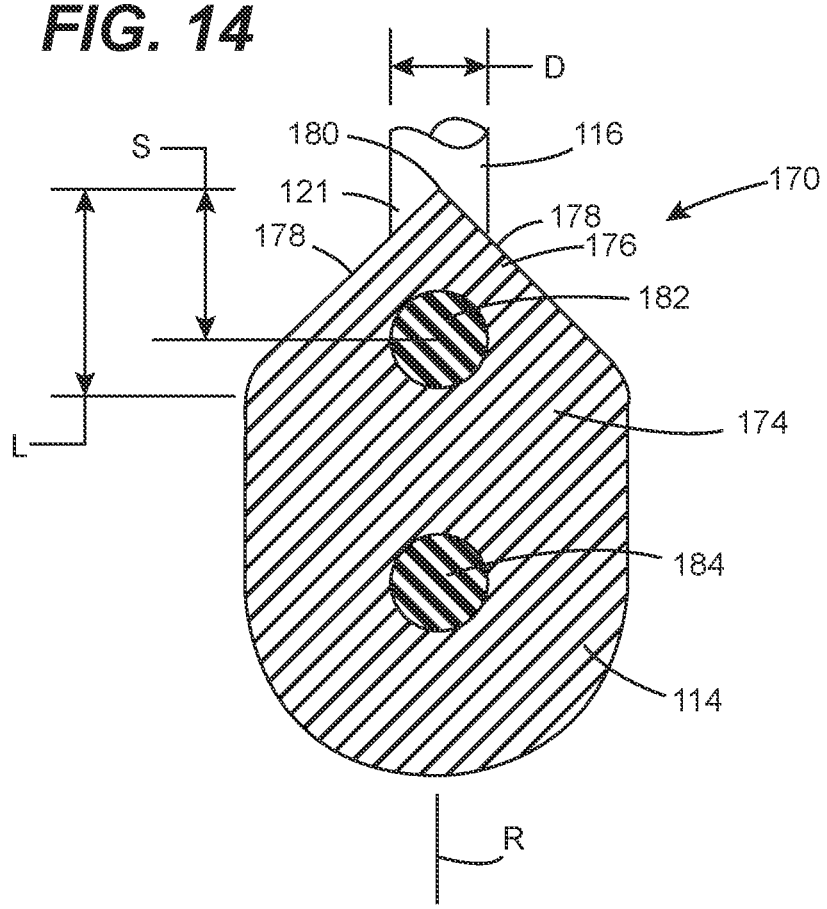
FIG. 14 is a cross-sectional view taken along the line 14-14 in FIG. 12.
Figure 15:
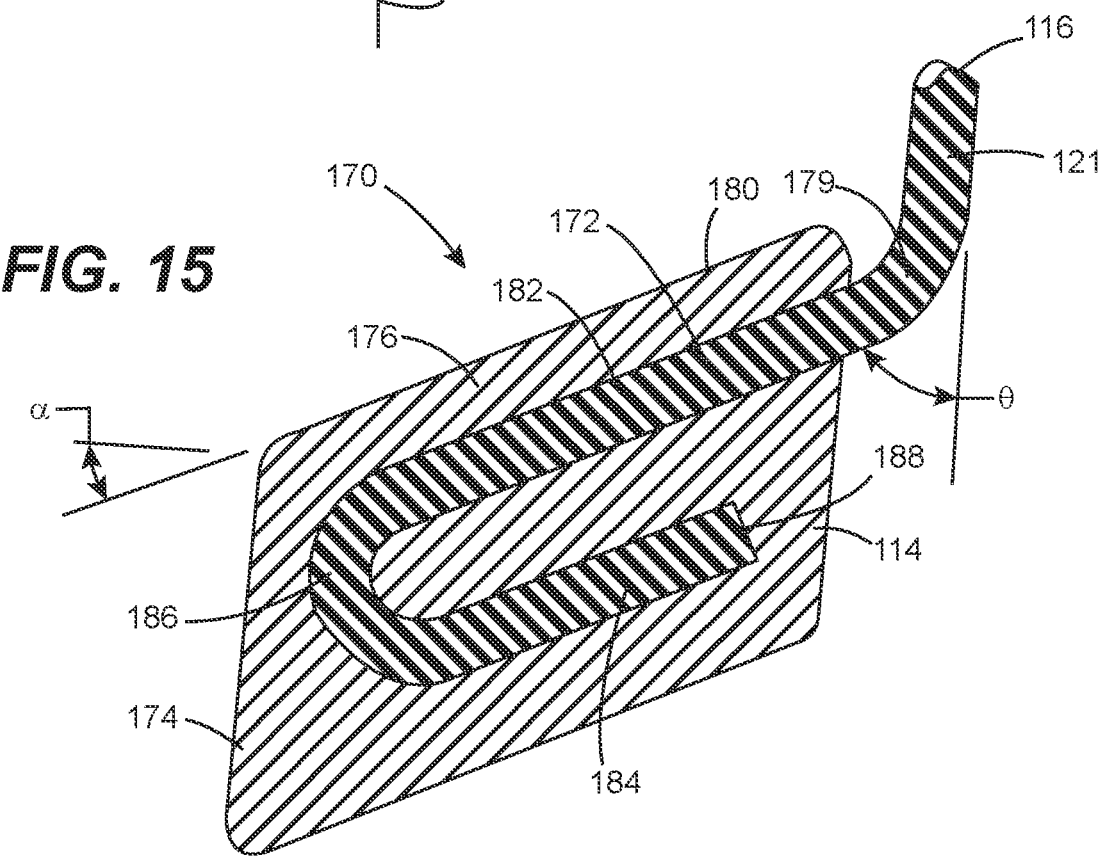
FIG. 15 is a cross-sectional view taken along the line 15-15 in FIG. 12.

The inventors have discovered that the relative position of cleaning members and coupling elements of wiper assemblies in accordance with embodiments of the present invention offer superior cleaning efficacy. In preferred embodiments, as shown in FIGS. 12-15, such superior cleaning efficacy results from a relative position and structural configuration of the cleaning member engaging structure 172 of the coupling element 116 relative to the wiping edge 180 of the cleaning member 114. More specifically, an entire portion of the first leg portion 182 is preferably within the blade portion 176 (i.e., located within a cross-sectional area of the blade portion 176) and an entire portion of the second portion 182 is preferably within the main body 174. As best shown in FIG. 15, the cleaning member engaging structure 172 preferably has a round cross-sectional shape and, as a result of the opposing angled faces 178 of the blade portion 176, the blade portion 176 has a generally triangular cross-sectional shape. In a preferred embodiment, a diameter D of the cleaning member engaging structure 172 is about 40% of an overall length L of the blade portion 176 and is centrally-located within the cross-sectional area of the blade portion 176. For example, as shown in FIG. 14, a set-back S of the first leg portion 182 can be approximately half the overall length L of the blade portion 176. In a specific preferred embodiment, as shown in FIG. 14, the opposing angled faces 178 of defining the blade portion 176 extend generally perpendicular to each other, the first and second leg portion 182, 184 each have a cross-sectional diameter D of about 0.026 inches, the blade portion 176 has an overall length L of about 0.065 inches and a reference R axis bisects the cleaning member 114 whereby the reference axis R extends through a centerline cross-sectional axis of the first and second legs 182, 184 of the cleaning member engaging structure 172 and through the wiping edge 180. Preferably, the reference axis R resides within a plane within which a longitudinal axis of a portion of the control element 116 extending between the proximate and distal end portions 106, 119 of the elongated member 102 resides. In the case of a cleaning member having an imaging element angle of nominally 90 degrees, the reference axis R will also extend generally parallel to the longitudinal axis L of the portion of the control element 116 extending between the proximate and distal end portions 106, 119 of the elongated member 102.

Components of cleaning apparatuses configured in accordance with embodiments of the present invention are not necessarily limited to particular materials or manufacturing methods. In one or more preferred embodiments, the coupling element 116 can be made from a metallic material such as, for example, stainless steel (e.g., 316 or 316 LVM stainless steel). In one or more preferred embodiments, the cleaning member 114 can be made from a polymeric material having elastomeric rubber, elastomeric-like or rubber-like properties (e.g., a two-part (e.g., transparent) silicone rubber having a durometer of about 60 Type A, a tensile strength of about 1300 psi, an elongation of about 525%, and a tear strength of about 250 ppi).

Thus, advantageously and beneficially, the wiper assembly 170 is characterized by at least a portion of the cleaning member engaging structure 172 encroaching into (preferably residing entirely within) a cross-sectional area of the blade portion 176 defined by the opposing angled faces 178. In this respect, the wiper assembly 170 is of a construction and a configuration that achieves deflection-defining aspects of the blade portion 176 as a function of both the material from which the cleaning member 114 is made and the presence of at least a portion of the cleaning member engaging structure 172 within the blade portion 176. The inventors of the present invention have discovered that such construction and a configuration provide a resulting synergistic functionality that leverages the bulk material and dimensional properties of the wiper assembly to enable a superior degree and reliability of cleaning efficacy provided by endoscope imaging element cleaning apparatuses in accordance with embodiments of the present invention and minimization of the physical size of such wiper assemblies.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. An apparatus, comprising:
a coupling element including a cleaning member engaging structure, wherein the cleaning member engaging structure includes a U-shaped portion defining a first leg portion of the cleaning member engaging structure and a second leg portion of the cleaning member engaging structure; and
a cleaning member having the cleaning member engaging structure residing therein, wherein the cleaning member includes opposing faces defining a blade portion thereof, wherein the blade portion extends from a main body of the cleaning member, wherein at least a portion of the first leg portion of the cleaning member engaging structure is within the blade portion and wherein at least a portion of the second leg portion of the cleaning member engaging structure is within the main body.

2. The apparatus of claim 1 wherein:
a portion of the first leg portion of the cleaning member engaging structure that is within the blade portion is entirely within the blade portion; and
an entire portion of the second leg portion is within the main body.

3. The apparatus of claim 1 wherein:
an arcuate segment of the U-shaped portion of the cleaning member engaging structure is partially within the blade portion and partially within the main body;
a first end portion of the arcuate segment is attached to the first leg portion; and
a second end portion of the arcuate segment is attached to the second leg portion.

4. The apparatus of claim 1 wherein:
the blade portion has a triangular cross-sectional shape; and
the first leg portion has a round cross-sectional shape.

5. The apparatus of claim 1 wherein a diameter of the first leg portion is at least about 40% of an overall length of the blade portion.

6. The apparatus of claim 1 wherein:
the opposing faces defining the blade portion extend generally perpendicular to each other; and
a reference axis extends through a centerline cross-sectional axis of the first leg of the cleaning member engaging structure, a centerline cross-sectional axis of the second leg of the cleaning member engaging structure and an intersecting point of the opposing faces.

7. The apparatus of claim 6 wherein:
the apparatus comprises a chassis; and
the reference axis is characterized by at least one of extending generally parallel to a longitudinal axis of a portion of the control element extending between the proximate and distal end portions of the chassis and residing within a plane within which the longitudinal axis of the portion of the control element extending between the proximate and distal end portions of the chassis resides.

8. An apparatus comprising:
a coupling element including a cleaning member engaging structure; and a cleaning member having at least a portion of the cleaning member engaging structure therein, wherein the cleaning member includes opposing faces defining a blade portion thereof and wherein at least a portion of the cleaning member engaging structure is within the blade portion, wherein:

the cleaning member engaging structure includes a plurality of segments that are spaced apart from each other; and at least a portion of a first one of the segments of the cleaning member engaging structure is within the blade portion;

a second one of the segments of the cleaning member engaging structure defines a distal end face of the coupling element;

the blade portion extends from a main body of the cleaning member; and at least a portion of the second one of the segments of the cleaning member engaging structure is within the main body, wherein:

the cleaning member engaging structure includes a U-shaped portion defining the first one of the segments of the cleaning member engaging structure and the second one of the segments of the cleaning member engaging structure;

an arcuate segment of the U-shaped portion of the cleaning member engaging structure is partially within the blade portion and partially within the main body;

a first end portion of the arcuate segment is attached to the first one of the segments of the cleaning member engaging structure; and a second end portion of the arcuate segment is attached to the second one of the segments of the cleaning member engaging structure.

9. An apparatus, comprising:

a coupling element including a wiper engaging structure, wherein the wiper engaging structure includes a U-shaped portion defining a first leg portion of the wiper engaging structure and a second leg portion of the wiper engaging structure; and a wiper having at least a portion of the wiper engaging structure residing therein, wherein the wiper includes opposing faces defining a blade portion thereof and wherein at least a portion of the first leg portion is within the blade portion, wherein the blade portion extends from a main body of the wiper and wherein at least a portion of the second leg portion is within the main body.

10. The apparatus of claim 9 wherein:

a portion of the first leg portion of the wiper engaging structure that is within the blade portion is entirely within the blade portion; and an entire portion of the second leg portion is within the main body.

11. The apparatus of claim 9 wherein:

an arcuate segment of the U-shaped portion of the wiper engaging structure is partially within the blade portion and partially within the main body;

a first end portion of the arcuate segment is attached to the first leg portion; and a second end portion of the arcuate segment is attached to the second leg portion.

12. The apparatus of claim 9 wherein:

the blade portion has a triangular cross-sectional shape; and the first leg portion has a round cross-sectional shape.

13. The apparatus of claim 9 wherein a diameter of the first leg portion is at least about 40% of an overall length of the blade portion.

14. The apparatus of claim 9 wherein:

the apparatus comprises a chassis;

the opposing faces defining the blade portion extend generally perpendicular to each other;

a reference axis extends through a centerline cross-sectional axis of the first leg of the wiper engaging structure, a centerline cross-sectional axis of the second leg of the wiper engaging structure and an intersecting point of the opposing faces; and the reference axis is characterized by at least one of extending generally parallel to a longitudinal axis of a portion of the control element extending between the proximate and distal end portions of the chassis and residing within a plane within which the longitudinal axis of the portion of the control element extending between the proximate and distal end portions of the chassis resides.

\* \* \* \* \*